US008883844B2

(12) United States Patent
Farber

(10) Patent No.: US 8,883,844 B2
(45) Date of Patent: Nov. 11, 2014

(54) NITRIC OXIDE RELEASING AMINO ACID ESTER FOR TREATMENT OF PULMONARY HYPERTENSION AND OTHER RESPIRATORY CONDITIONS

(75) Inventor: Michael Farber, Montreal (CA)

(73) Assignee: Nitrogenix Inc. (VG)

( * ) Notice: Subject to any disclaimer, the term of this patent is extended or adjusted under 35 U.S.C. 154(b) by 0 days.

(21) Appl. No.: 13/825,924

(22) PCT Filed: Sep. 22, 2011

(86) PCT No.: PCT/CA2011/001076
§ 371 (c)(1),
(2), (4) Date: Jun. 5, 2013

(87) PCT Pub. No.: WO2012/037665
PCT Pub. Date: Mar. 29, 2012

(65) Prior Publication Data
US 2014/0148438 A1    May 29, 2014

Related U.S. Application Data

(60) Provisional application No. 61/477,810, filed on Apr. 21, 2011, provisional application No. 61/386,444, filed on Sep. 24, 2010.

(51) Int. Cl.
| | | |
|---|---|---|
| A61K 31/40 | (2006.01) | |
| C07C 203/04 | (2006.01) | |
| A61K 9/00 | (2006.01) | |
| A61K 31/223 | (2006.01) | |
| A61K 45/06 | (2006.01) | |
| A61K 31/22 | (2006.01) | |

(52) U.S. Cl.
CPC ............. *C07C 203/04* (2013.01); *A61K 9/0078* (2013.01); *A61K 31/223* (2013.01); *A61K 45/06* (2013.01); *A61K 31/22* (2013.01)
USPC ........................................................ 514/424

(58) Field of Classification Search
None
See application file for complete search history.

(56) References Cited

U.S. PATENT DOCUMENTS

| | | | |
|---|---|---|---|
| 2,882,271 | A | 4/1959 | Janssen |
| 3,152,173 | A | 10/1964 | Ehrhart et al. |
| 3,261,859 | A | 7/1966 | Dengel |
| 3,262,977 | A | 7/1966 | Harsanyi et al. |
| 3,267,104 | A | 8/1966 | Hermans et al. |

(Continued)

FOREIGN PATENT DOCUMENTS

| | | |
|---|---|---|
| EP | 560 928 | 9/1997 |
| GB | 1025578 | 4/1966 |

(Continued)

OTHER PUBLICATIONS

Kovalchin, JP. et al., Nitric Oxide for Pulmonary Hypertension vol. 24, No. 4, 1997).*

*Primary Examiner* — San-Ming Hui
*Assistant Examiner* — Jeanmarie Calvillo
(74) *Attorney, Agent, or Firm* — Klauber & Jackson LLC

(57) ABSTRACT

There is provided compositions and methods for the treatment of respiratory conditions such as pulmonary hypertension and sickle-cell disease in a patient in need thereof. The composition and method are for treating a patient in need thereof by inhalation of a composition containing amino acid ester compounds comprising at least one nitric oxide releasing group and pharmaceutical salts thereof.

18 Claims, 1 Drawing Sheet

(56) References Cited

U.S. PATENT DOCUMENTS

| | | |
|---|---|---|
| 3,371,014 A | 2/1968 | Carlsson |
| 3,485,847 A | 12/1969 | Bossert et al. |
| 3,562,257 A | 2/1971 | Kugita et al. |
| 3,773,939 A | 11/1973 | Janssen |
| 3,799,934 A | 3/1974 | Meyer et al. |
| 3,962,238 A | 6/1976 | Mauvernay et al. |
| 3,985,758 A | 10/1976 | Murakami et al. |
| 4,154,839 A | 5/1979 | Wehinger et al. |
| 4,220,649 A | 9/1980 | Kojima et al. |
| 4,264,611 A | 4/1981 | Berntsson et al. |
| 4,338,322 A | 7/1982 | Sato |
| 4,446,325 A | 5/1984 | Ohno et al. |
| 4,466,972 A | 8/1984 | Neumann |
| 4,567,175 A | 1/1986 | Takeda et al. |
| 4,572,909 A | 2/1986 | Campbell et al. |
| 4,663,325 A | 5/1987 | Ohtaka et al. |
| 4,672,068 A | 6/1987 | Kutsuma et al. |
| 4,705,797 A | 11/1987 | Nardi et al. |
| 4,786,635 A | 11/1988 | Iwao et al. |
| 4,801,599 A | 1/1989 | Semeraro et al. |
| 4,808,605 A | 2/1989 | Branca et al. |
| 4,885,284 A | 12/1989 | Seto et al. |
| 4,892,875 A | 1/1990 | Meguro et al. |
| 4,952,592 A | 8/1990 | Torija et al. |
| 5,485,827 A | 1/1996 | Zapol et al. |
| 5,873,359 A | 2/1999 | Zapol et al. |
| 2005/0036949 A1 | 2/2005 | Tucker et al. |
| 2005/0228184 A1 | 10/2005 | Haj-Yehia |
| 2010/0076043 A1 | 3/2010 | Farber |

FOREIGN PATENT DOCUMENTS

| | | |
|---|---|---|
| WO | 92/10228 | 6/1992 |
| WO | 2008095841 | 8/2008 |
| WO | 2010/034118 | 4/2010 |
| WO | 2011/057386 | 5/2011 |
| WO | 2011/057387 | 5/2011 |

* cited by examiner

Fig. 1
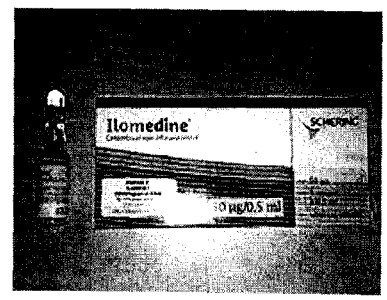
Fig. 2
 
Fig. 3A                               Fig. 3B

NITRIC OXIDE RELEASING AMINO ACID ESTER FOR TREATMENT OF PULMONARY HYPERTENSION AND OTHER RESPIRATORY CONDITIONS

CROSS REFERENCE TO RELATED APPLICATIONS

The present application is a National Stage Application claiming the priority of co-pending PCT Application No. PCT/CA2011/001076 filed Sep. 24, 2010, which in turn claims priority to U.S. Provisional application Ser. No. 61/386,444 filed Sep. 24, 2010, and Ser. No. 61/477,810 filed Apr. 21, 2011. Applicant claims the benefit of 35 U.S.C. '120 as to the PCT application and priority under 35 U.S.C. '119 as to the said United States provisional applications, and the entire disclosures of all referenced applications are incorporated herein by reference in their entireties.

BACKGROUND (a) Field

The subject matter disclosed generally relates to compositions and methods for the treatment of respiratory conditions, and more particularly to compositions and methods for treating pulmonary hypertension, acute chest syndrome and other symptoms of sickle-cell diseases, as well as other respiratory conditions, comprising an amino acid ester compound and a inhalable carrier.

(b) Related Prior Art

Nitric oxide relaxes pulmonary vessels, in particular when they are constricted by various disorders. Nitric oxide also relaxes airway smooth muscle and inhalation of exogenous nitric oxide attenuates airway constriction in the response to various agents in laboratory animals and humans. Thus, for instance EP 560 928, U.S. Pat. No. 5,485,827, U.S. Pat. No. 5,873,359 and WO 92/10228 disclose the use of nitric oxide for treating bronchoconstriction and pulmonary vasoconstriction.

NO inhalation (INO) is an efficient therapy in patients respiratory conditions such as pulmonary hypertension and acute chest syndrome. However, around ⅓ of the patients are hypo- or non-responders to INO. In addition thereto, worsening of the pulmonary hypertension and of the oxygenation have been observed during attempts to withdraw INO, which is termed rebound response. Life-threatening hemodynamic instability and deaths by discontinuing inhalation of nitric oxide have also been reported. Stepwise lowering of the NO dose will prolong the NO therapy but may still not eliminate the rebound response.

Sickle-cell disease is an autosomal recessive disorder and the most common genetic disease affecting African-Americans. Approximately 0.15% of African-Americans are homozygous for sickle cell disease, and 8% have sickle cell trait. Acute pain crisis, acute chest syndrome (ACS), and secondary pulmonary hypertension are common complications of sickle-cell disease. Pulmonary hypertension has now been identified as a major cause of death in adults with sickle cell disease. Common treatments for sickle-cell disease in children and young adults are continuous antibiotic therapy, use of hydroxyurea to lessen the acute chest syndrome, both of which have major side effects. Sickle cell is characterized by acute chest syndrome wherein deformed blood cells cannot pass through the constricted capillaries in the lungs and blockages occur causing severe pain and even death. These episodes were thought to be rare, but recent research shows that small episodes are an almost constant problem in the affected individuals.

Current research has also shown a direct link to the lack of nitric oxide and vasodilation in this acute state. Scavenging of nitric oxide by hemoglobin and disruption of nitric oxide release function contribute to the acute state in sickle-cell disease. Inhaled nitric oxide (NO) has been proposed as a possible therapy for both primary and secondary pulmonary hypertension. Furthermore, a number of recent studies have suggested that NO may have a favorable impact on sickle red cells at the molecular level and could improve the abnormal microvascular perfusion that is characteristic of sickle-cell disease. In addition, chronic exchange transfusion therapy may reduce the progression and/or severity of pulmonary hypertension in these patients. However nitric oxide gas administration is cumbersome, costly and can only be done in intensive care units with vigilance since over administration can be toxic. Also, a disadvantage of nitric oxide gas is that it has only a small penetration into tissue as it is reactive and has very short half life. A commonly used alternative is the use of nitroglycerin. However, there are several drawbacks to the manufacture, storage and use of nitroglycerin. Nitroglycerin is an explosive compound that is difficult to produce and stabilize. It is inherently unstable over the long term resulting in a maximum shelf life of a product containing of about six months.

Nitroprusside is another alternative compound that can be used to release NO to effect peripheral vasodilation in arterioles and venules, but the compound has the disadvantage of decomposing into very toxic cyanide ions.

A major drawback to the long term usage of nitroglycerin for the treatment of diseases is that the metabolic pathway for the liberation of nitric oxide from nitroglycerin occurs in the mitochondria, utilizing the aldehyde dehydrogenase 2 enzyme. The liberation of large amounts of nitric oxide within the mitochondria from the use of nitroglycerin proves to be toxic to the mitochondria over time and eventually causes extensive metabolic disruption. Also, certain classes of patient suffering from nitric oxide deficiencies, mainly of Asian descent, have been shown to carry a recessive allele of the gene producing aldehyde dehydrogenase 2 which renders them non-responsive to the use of nitroglycerin. Therefore, there is a need for alternative compounds to nitroglycerin and nitroprusside.

It is thus desirable to provide a composition and method for the treatment of pulmonary diseases which contains an alternative compound than gaseous NO, nitroglycerin or nitroprusside, and does not require any special operational procedures other than the inhalation of a composition.

It is also desirable to provide a composition and method for the treatment of pulmonary diseases which contains an alternative compound than gaseous NO, nitroglycerin or nitroprusside, and that lessens the rebound response when discontinuing inhalation of nitric oxide.

It is also desirable to provide a composition that can alter or at least improve the nitric oxide levels in the lungs of sickle-cell disease and acute chest syndrome sufferers while providing longer lasting prophylaxis than the few minutes afforded by nitric oxide gas infusion.

It is thus desirable to provide a method for the treatment of sickle-cell disease and/or acute chest syndrome which contains an alternative compound than gaseous NO or nitroglycerin, and does not require any special operational procedures other than the inhalation of a composition.

SUMMARY

In a first embodiment there is disclosed an inhalable composition comprising:
a therapeutically effective amount of a compound of formula (I):

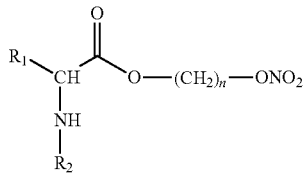

wherein n=1 to 10;
wherein $R_1$ is chosen an amino acid side chain group (D or L configuration),
wherein $R_2$ is a hydrogen atom, or an amino acid (D or L configuration), forming a peptide bond,
or any pharmaceutically acceptable salts thereof; and
in association with a pharmaceutically acceptable inhalable carrier.

The $R_1$ may be chosen from:
H,

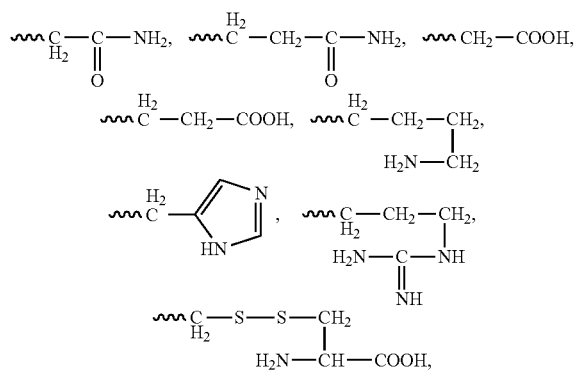

proline side chain,

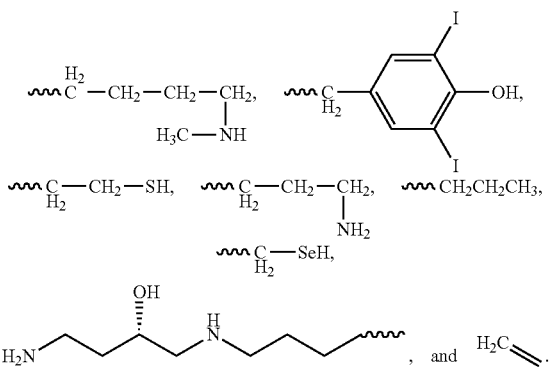

The $R_2$ may be an amino acid of formula (II) (D or L configuration) forming a peptide bond:

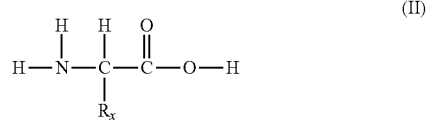

wherein $R_x$ is chosen from
H,

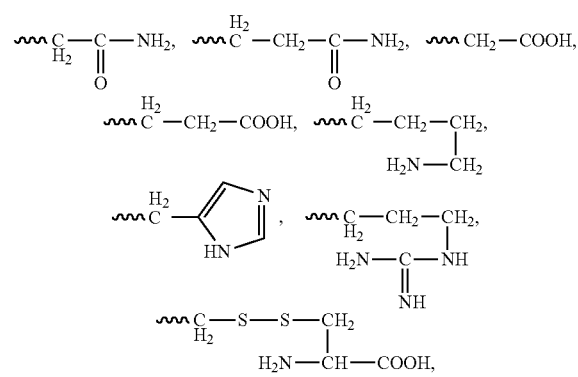

proline side chain,

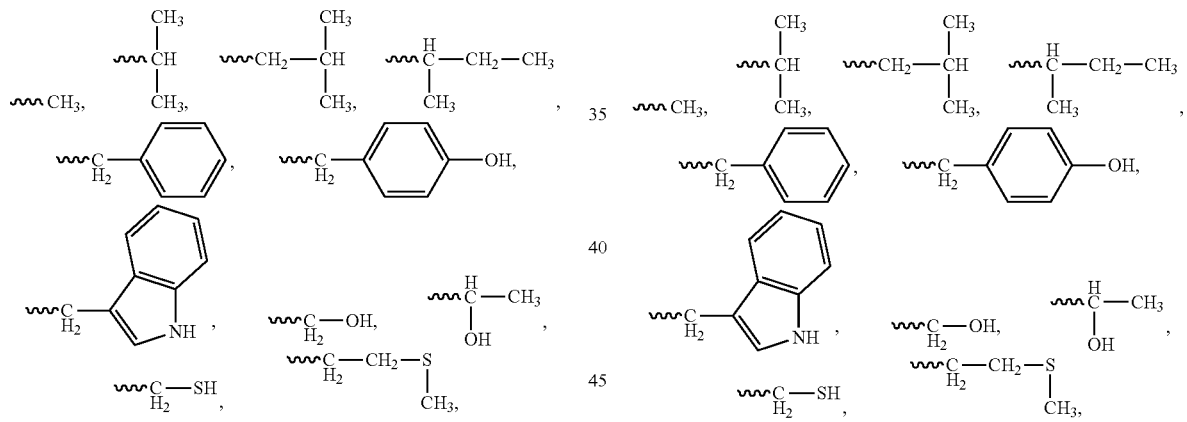

hydroxyproline side chain,

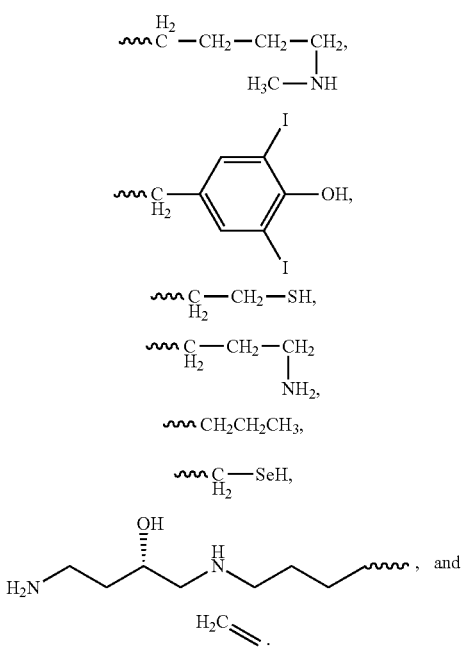

The compound of formula (I) may be (2-nitrooxy)-2-ethylamino-3-methylbutanoate:

or any pharmaceutically acceptable salts thereof.

The compound of formula (I) may be valine butylene glycol nitrate:

or any pharmaceutically acceptable salts thereof.

The compound of formula (I) may be 2'-nitrooxyethyl 2-amino-pentanoate:

or any pharmaceutically acceptable salts thereof.

The compound of formula (I) may be 4'-nitrooxybutyl 2-amino-pentanoate:

or any pharmaceutically acceptable salts thereof.

The compound of formula (I) may be:

or any pharmaceutically acceptable salts thereof.

The $R_2$ may be a hydrogen atom.

The composition may further comprise a cyclooxygenase inhibitor.

The cyclooxygenase inhibitor may be at least one of diclofenac, aceclofenac, nabumetone; meloxicam, meclofenamic, nimesulide; paracetamol; rofecoxib, celecoxib, DuP 697; GR 32191; flosulide; NS 398; L-745,337, DFU, HN-56249, JTE-552, aspirin, indometacin, and ibuprofen, or any pharmaceutically acceptable salts thereof.

The composition may further comprise an endothelin receptor antagonist, and the endothelin receptor antagonist may be at least one of bosentan, ambrisentan, sitaxsentan, and TBC3711.

The composition may further comprise a phosphodiesterase (PDE) inhibitor. The phosphodiesterase (PDE) inhibitor may be at least one of enoximone, milrinone, Amrinone, sildenafil, tadalafil and vardenafil. The phosphodiesterase inhibitor may be ibudilast.

The composition may further comprise epoprostenol (prostacyclin).

The composition may further comprise an epoprostenol derivative. The epoprostenol derivative may be at least one of treprostinil, beraprost and iloprost.

The composition may further comprise a bronchodilator. The bronchodilator may be at least one of pirbuterol, epinephrine, salbutamol (albuterol), salmeterol, levosalbutamol (levalbuterol) and clenbuterol.

The composition may further comprise a calcium channel blocker. The calcium channel blocker may be at least one of amlodipine, bepridil, clentiazem, diltiazem, fendiline, gallopamil, mibefradil, prenylamine, semotiadil, terodiline, verapamil, aranidipine, bamidipine, benidipine, cilnidipine, efonidipine, elgodipine, felodipine, isradipine, lacidipine, lercanidipine, manidipine, nicardipine, nifedipine, nilvadipine, nimodipine, nisoldipine, nitrendipine, cinnarizine, flunarizine, lidoflazine, lomerizine, bencyclane, etafenone, and perhexiline.

The pharmaceutically acceptable inhalable carrier may be chosen from an aqueous solvent, a non-aqueous solvent, and combinations thereof. The aqueous and non-aqueous solvent may be chosen from a polar solvent, a non-polar solvent, and combinations thereof.

The pharmaceutically acceptable inhalable carrier may be an inhalable dry powder.

The pharmaceutically acceptable inhalable carrier may be at least one of a microparticle and a microsphere.

The composition may be inhalable as an aerosol spray.

The composition may be inhalable as a mist.

In a second embodiment there is disclosed an inhalable composition delivery device comprising at least one dose of an inhalable composition according to the present invention and a propellant.

The inhalable composition delivery may be chosen from a metered-dose inhaler, a dry powder inhaler, a pump spray and a nebulizer.

In a third embodiment, there is disclosed a method of treating a pulmonary disease in a patient which comprises:
(a) treating said patient by inhalation with a therapeutically effective amount of an inhalable composition according to the present invention.

In another embodiment, there is disclosed a method of treating a pulmonary disease in a patient which comprises:
(a) treating said patient by inhalation with a therapeutically effective amount of an inhalable composition according to the present invention prior to or after treatment with a therapeutically effective amount of a COX inhibitor.

In another embodiment, there is disclosed a method of treating a pulmonary disease in a patient which comprises:
(a) treating said patient by inhalation with a therapeutically effective amount of an inhalable composition according to the present invention prior to or after treatment with a therapeutically effective amount of a phosphodiesterase inhibitor.

In another embodiment, there is disclosed a method of treating a pulmonary disease in a patient which comprises:
(a) treating said patient by inhalation with a therapeutically effective amount of an inhalable composition according to the present invention prior to or after treatment with a therapeutically effective amount of a bronchodilator.

In another embodiment, there is disclosed a method of treating a pulmonary disease in a patient which comprises:
treating said patient by inhalation with a therapeutically effective amount of an inhalable composition according to the present invention prior to or after treatment with a therapeutically effective amount of a calcium channel blocker.

In another embodiment, there is disclosed a method of treating a pulmonary disease in a patient which comprises:
(a) applying an inhalable composition delivery device according to the present invention to at least one of an oral cavity and a nasal cavity of said patient, and activating said inhalable composition delivery device to release a dose of inhalable composition contained therein.

The methods according to the present invention may further comprising administering to said patient nitric oxide gas prior to or after inhaling a therapeutically effective amount of the inhalable composition.

In the method according to the present invention, the pulmonary disease may be at least one of a sickle cell disease, a pulmonary hypertension, a pulmonary insufficiency, a cystic fibrosis, a chronic obstructive pulmonary disease, an Infant respiratory distress syndrome (IRDS), a pulmonary vasoconstriction, and an airway constriction.

The sickle cell disease may be associated with acute chest syndrome (ACS).

The pulmonary hypertension may be at least one of pulmonary venous hypertension (PVH) and pulmonary arterial hypertension (PAH).

The chronic obstructive pulmonary disease may be at least one of chronic bronchitis and emphysema.

The pulmonary vasoconstriction, airway constriction or both may be associated with a clinical condition resulting from at least one of a traumatic injury, a fat embolism in the lung, an acidosis, an adult respiratory distress syndrome, an acute mountain sickness, a post cardiovascular and pulmonary surgery, an acute pulmonary hypertension, a persistent pulmonary hypertension of the new-born, a perinatal aspiration syndrome, a hyaline membrane disease, an acute pulmonary thromboembolism, an acute pulmonary edema, an heparin-protamine reactions, a hypoxia and asthma bronchiale, an acute condition of asthma bronchiale and asthma asthmaticus.

The patient may have a normotensive blood pressure, a hypertensive blood pressure, or a hypotensive blood pressure.

In the methods according to the present invention, when blood pressure is a normotensive blood pressure or a hypotensive blood pressure, the treating of the patient by inhalation may result in a stable blood pressure.

In the methods according to the present invention, when said blood pressure is a hypertensive blood pressure, the treating of the patient by inhalation may result in a decreased blood pressure.

The decreased blood pressure may be a normotensive blood pressure.

In another embodiment, there is disclosed a use of a compound of formula (I) for the preparation of a medicament for treating a pulmonary disease:

$$R_1-\underset{\underset{R_2}{\overset{NH}{|}}}{\overset{}{CH}}-\overset{O}{\overset{\|}{C}}-O-(CH_2)_n-ONO_2 \qquad (I)$$

wherein n=1 to 10;

wherein $R_1$ is an amino acid side chain group (D or L configuration), wherein $R_2$ is a hydrogen atom, or an amino acid (D or L configuration) forming a peptide bond, or any pharmaceutically acceptable salts thereof.

In another embodiment, there is disclosed a use of a compound of formula (I) for the treatment of a pulmonary disease:

$$R_1-\underset{\underset{R_2}{\overset{NH}{|}}}{\overset{}{CH}}-\overset{O}{\overset{\|}{C}}-O-(CH_2)_n-ONO_2 \qquad (I)$$

wherein n=1 to 10;

wherein $R_1$ is an amino acid side chain group (D or L configuration), wherein $R_2$ is a hydrogen atom, or an amino acid (D or L configuration) forming a peptide bond, or any pharmaceutically acceptable salts thereof.

The $R_1$ may be chosen from:
H,
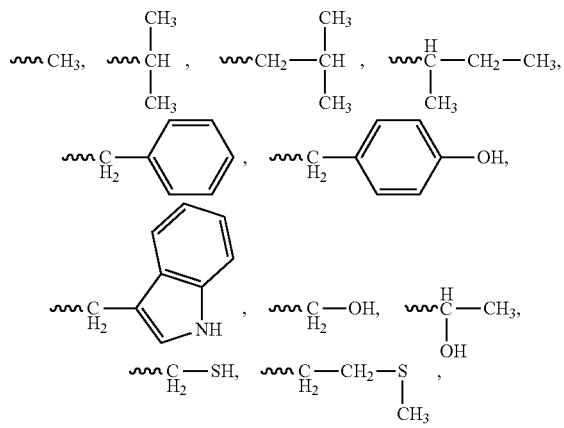
proline side chain,
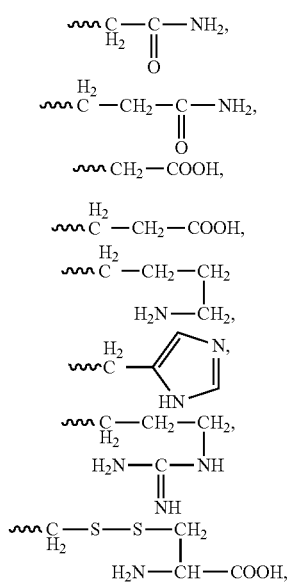
hydroxyproline side chain,
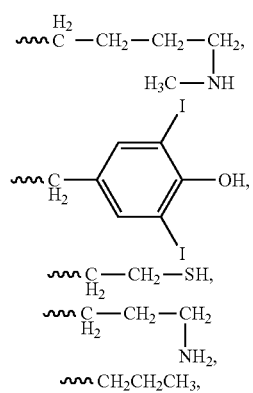
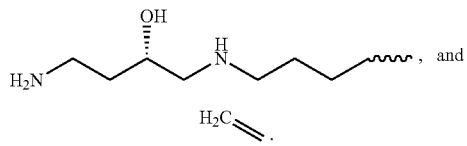
The $R_2$ may be an amino acid of formula (II) (D or L configuration) forming a peptide bond:
$$H-N\underset{R_x}{\overset{H}{-}C}-\overset{O}{\overset{\|}{C}}-O-H \qquad (II)$$
wherein $R_x$ is chosen from
H,
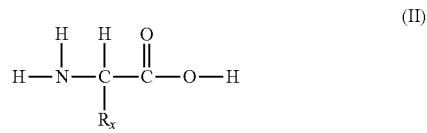
proline side chain, -continued

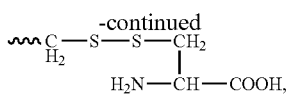

hydroxyproline side chain,

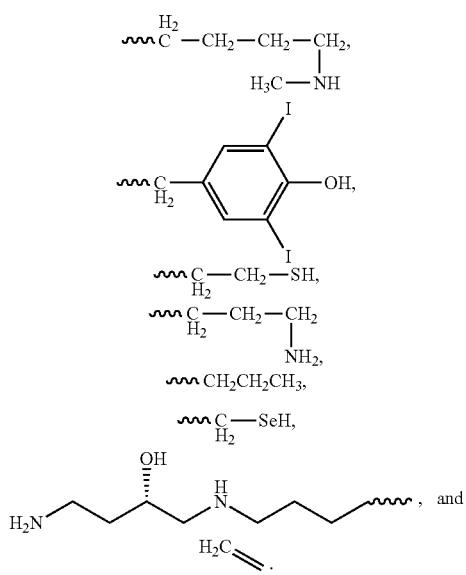

The compound of formula (I) may be (2-nitrooxy)-2-ethylamino-3-methylbutanoate:

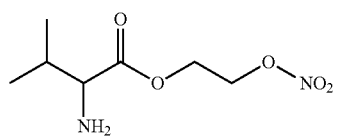

or any pharmaceutically acceptable salts thereof.

The compound of formula (I) may be valine butylene glycol nitrate:

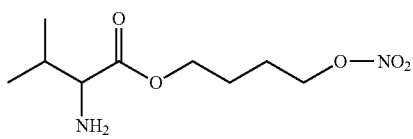 [SMILES: CC(C)C(N)C(=O)OCCCCO[N+](=O)[O-]]

or any pharmaceutically acceptable salts thereof.

The compound of formula (I) may be 2'-nitrooxyethyl 2-amino-pentanoate:

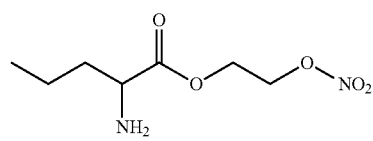

or any pharmaceutically acceptable salts thereof.

The compound of formula (I) may be 4'-nitrooxybutyl 2-amino-pentanoate:

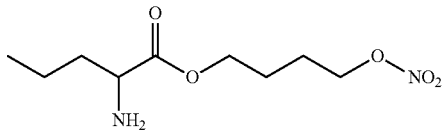 [SMILES: CCCC(N)C(=O)OCCCCO[N+](=O)[O-]]

or any pharmaceutically acceptable salts thereof.

The compound of formula (I) may be:

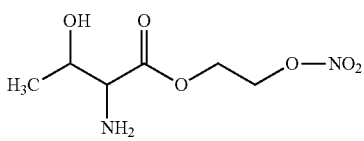

or any pharmaceutically acceptable salts thereof.

The $R_2$ may be a hydrogen atom.

The following terms are defined below.

The term "Amino acid ester compound" is intended to mean the condensation product of an amino acid with mono-nitrated alkane or alkene diol. As will be evident to those familiar to the art, the condensation reaction could also involve, but not limited to, dipeptides or tripeptides, nitrated alcohols containing aliphatic, alkyl or aromatic moieties, as well as other nitric oxide groups attached to the alkane or alkene diols. Amino acid or dipeptide reactions are preferred as well as the condensation reaction with short chain mono-nitrated alkane diols such as 1,3 propanediol or 1,4 butanediol.

The expression "Therapeutically effective amount" is intended to mean the amount of the compound and/or composition that is effective to achieve its intended purpose in a sense that is common within this technical field.

The terms "Carriers" or "vehicles" are intended to mean carrier materials suitable for compound administration and include any such material known in the art such as, for example, any liquid, lotion, gel, solvent, liquid diluent, solubilizer, gas or the like, which is non-irritating.

The term "Nitric oxide adduct" or "NO adduct" is intended to mean compounds and functional groups which, under physiological conditions, can donate, release and/or directly or indirectly transfer any of the three redox forms of nitrogen monoxide ($NO^+$, $NO^-$, NO.), such that the biological activity of the nitrogen monoxide species is expressed at the intended site of action.

The term "Nitric oxide releasing" or "nitric oxide donating" is intended to mean methods of donating, releasing and/or directly or indirectly transferring any of the three redox forms of nitrogen monoxide (NO+, NO−, NO.), such that the biological activity of the nitrogen monoxide species is expressed at the intended site of action.

The term "Nitric oxide donor" or "NO donor" is intended to mean compounds that donate, release and/or directly or indirectly transfer a nitrogen monoxide species, and/or stimulate the endogenous production of nitric oxide or endothelium-derived relaxing factor (EDRF) in vivo and/or elevate endogenous levels of nitric oxide or EDRF in vivo and/or are oxidized to produce nitric oxide and/or are substrates for nitric oxide synthase and/or cytochrome P450. "NO donor" also includes compounds that are precursors of L-arginine, inhibitors of the enzyme arginase and nitric oxide mediators.

The term "pharmaceutical acceptable inhalable carrier" is intended to mean a preservative solution, a saline solution, an isotonic (about 0.9%) saline solution, or about a 5% albumin solution, suspension, sterile water, phosphate buffered saline, and the like. It is also intended to mean any aqueous or non-aqueous solvents that are suitable for delivery of medicine into the lungs, as described herein. It is also intended to mean any dry powder, microparticles or microspheres that are suitable for delivery of medicine into the lungs. Other buffering agents, dispersing agents, and inert non-toxic substances suitable for delivery to a patient may be included in the compositions of the present invention. The compositions may be solutions, suspensions or any appropriate formulation suitable for administration, and are typically sterile and free of undesirable particulate matter. The compositions may be sterilized by conventional sterilization techniques.

The term "inhalation" is intended to mean the movement of air from the external environment, through the air ways, and into the alveoli. To inhale is also known as inspiration.

Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

BRIEF DESCRIPTION OF THE DRAWINGS

Further features and advantages of the present disclosure will become apparent from the following detailed description, taken in combination with the appended drawings, in which:

FIG. 1 illustrates a example of a nebulizer device as used with the present invention.

FIG. 2 illustrates an ampoule containing a compound to be dissolved in a solvent (e.g. water) and nebulized in a nebulizer device.

FIGS. 3A and 3B illustrate devices permitting inhalation of medication through A) both the oral and nasal cavity and B) the oral cavity.

DETAILED DESCRIPTION OF THE PREFERRED EMBODIMENTS

The composition of the present invention contains vasoactive amino acid ester compounds. The nitric oxide amino acid ester compounds of the present invention possess many of the required characteristics necessary to fulfill the role of a primary boosting of NO levels. The compounds easily dissociate in water into the amino acid derivative and associated ion forming the pharmaceutical salt. The compounds of the present invention are extremely stable in the form of the salts, and thus possess long shelf lives and stability.

The nitric oxide releasing groups of the compounds of the present invention are preferably nitro groups (i.e. $NO_2$), nitroso groups (i.e. NO) and/or heterocyclic nitric oxide donor groups that are linked to the amino acid ester compounds through one or more sites such as oxygen (hydroxyl condensation), sulfur (sulfhydryl condensation) and/or nitrogen. The heterocyclic nitric oxide donor groups are preferably furoxans, sydnonimines, oxatriazole-5-ones and/or oxatriazole-5-imines.

The preferred compounds of the present invention are the valine or norvaline derivatives of the nitric oxide amino acid ester of the present invention. The most preferred compounds are known as valine nitrooxy ethyl ester (or valine ethylene glycol nitrate), valine nitrooxy butyl ester (or valine butylene glycol nitrate) or any pharmaceutically acceptable salts thereof, which possess many of the required characteristics necessary to fulfill the role of boosting NO levels. The compound easily dissociates in water into the valine derivative valine ethylene or butylene glycol nitrate and the salt forming acid. The compounds are extremely stable in the form of the salt and thus possess a long shelf life. It has been observed that the preferred compounds of the present invention do not cause hypotension in normotensive or hypotensive individuals. Therefore, upon administration of the preferred compounds of the present invention, an hypertensive individual will experience the vasodilatory effect caused by the preferred compounds, which will result in a decrease in blood pressure. The decrease in blood pressure may be up to a normotensive blood pressure. Individuals with normal blood pressure will not experience the vasodilatory effect caused by the preferred compounds, and their blood pressure will remain stable (unchanged). Individuals with lower than normal blood pressure (hypotensive) will not experience a further drop in blood pressure and their blood pressure will remain stable (unchanged). Furthermore, the preferred compounds of the present invention have half-life of approximately 5 hours. Preferably, a therapeutically effective amount of the compounds of the present invention are administered. Therapeutically effective amounts include but are not limited to 0.5 to 30 mg of the compound of the present invention. Preferably, therapeutically effective amounts include 1 to 15 mg, 0.5 to 5 mg, 1 to 5 mg, 5 to 10 mg, 10 to 15 mg, 1 to 15 mg, 1 to 30 mg, 5 to 20 mg, 5 to 15 mg, 5 to 30 mg, 10 to 20 mg, 10 to 30 mg and 15 to 30 mg.

The compounds and compositions of the invention can be formulated as pharmaceutically acceptable salt forms. Pharmaceutically acceptable salts include, for example, alkali metal salts and addition salts of free acids or free bases. The nature of the salt is not critical, provided that it is pharmaceutically-acceptable. Suitable pharmaceutically-acceptable acid addition salts may be prepared from an inorganic acid or from an organic acid. Examples of such inorganic acids include, but are not limited to, hydrochloric, hydrobromic, hydroiodic, nitric, carbonic, sulfuric and phosphoric acid and the like. Appropriate organic acids include, but are not limited to, aliphatic, cycloaliphatic, aromatic, heterocyclic, carboxylic and sulfonic classes of organic acids, such as, for example, formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, stearic, algenic, β-hydroxybutyric, cyclohexylaminosulfonic, galactaric and galacturonic acid and the like. Suitable pharmaceutically-acceptable base addition salts include, but are not limited to, metallic salts made from aluminum, calcium, lithium, magnesium, potassium, sodium and zinc or organic salts made from primary, secondary and tertiary amines, cyclic amines, N,N'-dibenzylethylenediamine, chloroprocaine, choline, diethanolamine, ethylenediamine, meglumine (N-methylglucamine) and procaine and the like. All of these salts may be prepared by conventional means from the corresponding compound by reacting, for example, the appropriate acid or base with the compound. In one embodiment, the pharmaceutically acceptable salts of the compounds of the invention include the nitrate salts. In another embodiment, the pharmaceutically acceptable salts of the compounds of the invention are heterocyclic compounds such as, furoxan, a sydnonimine, an oxatriazole-5-one and/or an oxatriazole-5-imine.

The compounds of the present invention, because of the small size of the molecule, can be other choices of linkages and/or amino acids or their derivatives. For example, as alternatives to the above choices, propyl, butyl, or longer chains may be linked to any amino acid. Salts such as chloride or hydrochloride salts may be used. Other amino acid derivatives may also be chosen. Derivatives of the base amino acids whether they are in the L or D configuration of these amino acids can be chosen. Non standard amino acids, or synthetic derivative of standard and non-standard amino acids may be elected, such as those containing acetyl groups attached to the amide of the molecule or nor derivatives of the amino acids, when such derivatives can be achieved.

The amino acid esters compounds may be based on natural, non-standard or even modified amino acids, with the basic structure as depicted below, where the $R_x$ represents the side chain of the amino acid (wherein $R_x$ may be $R_1$, $R_2$ or $R_3$, as applicable to the specific molecule described herein):

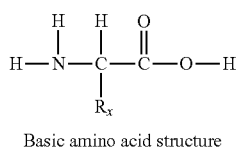

Basic amino acid structure

Natural Amino Acids

| N° | Originating Amino acid | Formula | $R_x = R_1$ or $R_2$ |
|---|---|---|---|
| 1 | Glycine | H | —H |
| 2 | Alanine | $CH_3$ | $\sim\!\!\sim CH_3$ |
| 3 | Valine* | $CH(CH_3)_2$ | $\sim\!\!\sim CH(CH_3)_2$ |
| 4 | Leucine* | $CH_2CH(CH_3)_2$ | $\sim\!\!\sim CH_2CH(CH_3)_2$ |
| 5 | Isoleucine* | $CH(CH_3)CH_2CH_3$ | $\sim\!\!\sim CH(CH_3)CH_2CH_3$ (structure) |
| 6 | Phenylalanine* | $CH_2C_6H_5$ | $\sim\!\!\sim CH_2-C_6H_5$ |
| 7 | Tyrosine | $CH_2C_6H_4OH$ | $\sim\!\!\sim CH_2-C_6H_4-OH$ |
| 8 | Tryptophane* | $C_9H_8N$ | (indole structure) |
| 9 | Serine | $CH_2OH$ | $\sim\!\!\sim CH_2-OH$ |
| 10 | Threonine* | $CH(OH)CH_3$ | $\sim\!\!\sim CH(OH)CH_3$ |
| 11 | Cysteine | $CH_2SH$ | $\sim\!\!\sim CH_2-SH$ |
| 12 | Methionine* | $CH_2CH_2SCH_3$ | $\sim\!\!\sim CH_2-CH_2-S-CH_3$ |
| 13 | Proline | $C_5H_9NO_2$ | (pyrrolidine-COOH structure) |
| 14 | Asparagine | $CH_2COCH_2$ | $\sim\!\!\sim CH_2-C(=O)-NH_2$ |
| 15 | Glutamine | $CH_2CH_2CONH_2$ | $\sim\!\!\sim CH_2-CH_2-C(=O)-NH_2$ |
| 16 | Aspartic acid | $CH_2COOH$ | $\sim\!\!\sim CH_2-COOH$ |
| 17 | Glutamic acid | $CH_2CH_2COOH$ | $\sim\!\!\sim CH_2-CH_2-COOH$ |
| 18 | Lysine* | $CH_2CH_2CH_2CH_2NH_2$ | $\sim\!\!\sim CH_2-CH_2-CH_2-CH_2-NH_2$ |
| 19 | Histidine* | $CH_3C_3N_2H_3$ | (imidazole structure) |
| 20 | Arginine* | $(CH_2)_3CN_3H_4$ | $\sim\!\!\sim CH_2-CH_2-CH_2-NH-C(=NH)-NH_2$ |

*essential amino acids

Modified Amino Acids

| N° | Originating Amino acid | Formula | $R_x = R_1$ or $R_2$ |
|---|---|---|---|
| A | Cystine | $CH_2S_2CH_2CHNH_2COOH$ |  |

-continued

| | Modified Amino Acids | | | |
|---|---|---|---|---|
| N° | Originating Amino acid | Formula | | $R_x = R_1$ or $R_2$ |
| B | Hydroxyproline | $C_5H_9NO_3$ | | (pyrrolidine with HO and COOH) |
| C | ε-N-methyllysine | $CH_2CH_2CH_2CH_2NHCH_3$ | | $\sim C H_2 - CH_2 - CH_2 - CH_2$ with $H_3C-NH$ |
| D | diiodotyrosine | $CH_2C_6H_2I_2OH$ | | (diiodophenol structure) |
| E | homocysteine | $CH_2CH_2SH$ | | $\sim CH_2 - CH_2 - SH$ |
| F | ornithine | $CH_2CH_2CH_2NH_2$ | | $\sim CH_2 - CH_2 - CH_2$ with $NH_2$ |
| G | Norvaline | $CH_2-CH_2-CH_3$ | | $\sim CH_2CH_2CH_3$ |
| H | selenocysteine | $CH_2-SeH$ | | $\sim CH_2 - SeH$ |
| I | Hypusine | $CH_2CH_2CH_2CH_2NHCH_2CH(OH)CH_2CH_2NH_2$ | | (OH-substituted diamine structure) |
| J | Dehydroalanine | $CH_2$ | | $H_2C=$ |

The nitric oxide amino acid ester compounds of the present invention are not limited to a single amino acid molecule. The compounds of the present invention may be dipeptide or even tripeptide molecules, with the general formula depicted below and where $R_x$ and $R_y$ independently are any of the amino acid side chains described herein.

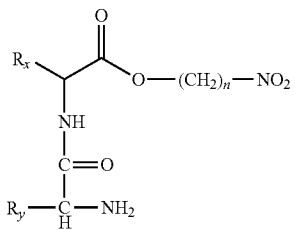

The composition containing a compound as defined in the present invention may include a wide variety of additional components, including, for example, one or more of gases, gaseous precursors, liquids, oils, stabilizing materials, pharmaceutical acceptable carriers, photoactive agents.

In an embodiment of the present invention, a combination therapy is disclosed for treating pulmonary hyperthension, sickle cell disease and the associated acute chest syndrome, or other pulmonary diseases. In one aspect of this embodiment, a pharmaceutical agent other than a nitric oxide amino acid ester according to the present invention is administered to a patient in addition to the nitric oxide amino acid ester compound(s). The delivery means may be any means discussed herein that is suitable for the delivery of the combination of nitric oxide amino acid ester compound(s) and the other pharmaceutical agent. The other pharmaceutical agent may be contained in the same composition as the nitric oxide amino acid ester compound(s) or it may be in a separate composition. Alternatively, the other pharmaceutical agent may be administered in a form other than a inhalable composition. The other pharmaceutical agent may be administered orally, bucally, sublingually, parenterally, transdermally, rectally, topically, intramuscularly, intravenously, or by injection, as known in the art, and as may be required by the specific other pharmaceutical agent. The other pharmaceutical agent may be administered at the same time as the composition comprising the nitric oxide amino acid ester compound(s) or may be administered at any desired time before and/or after administration of the microparticles comprising the nitric oxide amino acid ester compound(s).

Other Pharmaceutical Agent

Endothelin Receptor Antagonists (ETRA)

In one embodiment, the pharmaceutical agent other than a nitric oxide amino acid ester compound may be an endothelin receptor antagonist that modulates the vasostate (e.g., vasodilation) of blood vessels. Preferably, the endothelin receptor antagonist is selected from the group consisting of bosentan (Tracleer™, Actelion), ambrisentan (Myogen) and sitaxentan (Encysive Pharmaceuticals).

In some embodiments, the pharmaceutical agent which is administered in addition to a nitric oxide amino acid ester compound is an endothelin receptor antagonist. There is increasing evidence that endothelin-1 has a pathogenic role in pulmonary arterial hypertension and that blockade of endothelin receptors may be beneficial. Endothelin-1 is a potent endogenous vasoconstrictor and smooth-muscle mitogen that is overexpressed in the plasma and lung tissue of patients with pulmonary arterial hypertension. There are two classes of endothelin receptors: Endothelin A, ET-A and Endothelin B, ET-B receptors, which play significantly different roles in regulating blood vessel diameter. The binding of endothelin to ET-A receptors located on smooth muscle cells causes vasoconstriction, whereas the binding of endothelin to ET-B receptors located on the vascular endothelium causes vasodilatation through the production of nitric oxide. This latter activity of the ET-B receptor is thought to be counter-regulatory and protects against excessive vasoconstriction.

Therefore, another attractive approach to treating pulmonary hypertension has been the blockade of these endothelin receptors. Two types of ETRAs have been developed: dual ETRAs, which block the receptors for both ET-A and ET-B, and selective ETRAs, which block only the ET-A receptor.

Dual Endothelin Receptor Antagonist

The first generation ETRAs are non-selective and block both the ET-A and ET-B receptors. Bosentan (Tracleer™) is the first FDA approved ETRA (see U.S. Pat. No. 5,292,740). Two placebo controlled trials of bosentan (an endothelin receptor A and B antagonist) have been conducted. The six minute walk test improved in the whole group, but the improvement was greater when the drug was used in higher doses. However, liver toxicity occurred with the higher dose.

Selective Endothelin Receptor Antagonist

Second generation ETRAs bind to the ET-A receptor in preference to the ET-B receptor. Currently, there are two selective ETRAs in clinical trials: sitaxsentan and ambrisentan (BSF 208075). A pure endothelin A antagonist, sitaxsentan has been used in an open pilot study. This showed an improvement in the six minute walk test and a decrease in pulmonary vascular resistance of 30%. A more potent endothelin compound, TBC3711 (Encysive Pharmaceuticals), entered Phase I testing in December 2001. This drug holds potential for treating chronic heart failure and essential hypertension.

There are small clinical trials of using bosentan in patients that are already on other medications for the treatment of pulmonary hypertension. In a preferred embodiment of the present invention, the combination therapy comprises a nitric oxide amino acid ester compound and bosentan acting in combination through distinct mechanisms of action, preferably synergistically, to treat pulmonary hypertension. In yet another preferred embodiment, a nitric oxide amino acid ester compound is combined with sitaxentan. In yet another embodiment, a nitric oxide amino acid ester compound is combined with ambrisentan. In yet another embodiment a nitric oxide amino acid ester compound is aerosolized and administered in combination with bosentan, or sitaxsentan, or ambrisentan. In another embodiment, a nitric oxide amino acid ester compound is combined with TBC3711 in combination therapy of pulmonary hypertension.

Modulator of Prostacyclin Activity

In another embodiment, the pharmaceutical agent to be administered in addition to a nitric oxide amino acid ester compound is a pharmaceutical agent which modulates prostacyclin activity, bioavailability, half-life, or ameliorates an undesirable side-effect of the prostacyclin. In one preferred embodiment, the pharmaceutical agent to be administered in addition to a nitric oxide amino acid ester compound is a PDE inhibitor adapted to enhance the prostacyclin activity, preferably chosen from enoximone, milrinone (Primacor®), Amrinone (Inocor®), sildenafil (Viagra®), tadalafil (Cialis®) and vardenafil (LEVITRA®).

Epoprostenol Derivatives

In some embodiments, the pharmaceutical agent to be administered in addition to a nitric oxide amino acid ester compound is an epoprostenol (prostacyclin) or a derivative thereof (such as iloprost). A continuous infusion of prostacyclin (Flolan®, GlaxoSmithKline) was the first therapy shown to reduce mortality in a controlled study of patients with severe pulmonary hypertension. However, its use is associated with a number of serious drawbacks. The lack of pulmonary selectivity results in systemic side effects, tolerance leads to progressive increases in the dose, and there may be recurrent infections of the intravenous catheter. As an alternative, inhaled nitric oxide possesses pulmonary selectivity, but it is less potent than prostacyclin in the pulmonary vasculature. Moreover, an interruption in the inhalation of continuous nitric oxide may cause rebound pulmonary hypertension. Designed to combine the beneficial effects of prostacyclin with those of an inhalational application, aerosolized prostacyclin was found to be a potent pulmonary vasodilator in patients with acute respiratory failure, exerting preferential vasodilatation in well-ventilated lung regions. Similar results were obtained in spontaneously breathing patients who had lung fibrosis and severe pulmonary hypertension.

Three epoprostenol analogs have been studied in the treatment of PAH: treprostinil (Remodulin®, United Therapeutics), beraprost, and iloprost. Treprostinol is a stable analogue of epoprostenol, which is given continuously subcutaneously. Escalation of dosage has been limited by significant infusion site pain. Thus many patients do not receive therapeutic doses. Beraprost is active orally and has shown a benefit in a study in PAH at 3 and 6 months but not at 9 or 12 months.

Nitric Oxide Production

In some embodiments, the pharmaceutical agent which is administered in addition to a nitric oxide amino acid ester compound is nitric oxide or a pharmaceutical agent which is a substrate for nitric oxide. Endothelial production of nitric oxide is diminished with pulmonary hypertension, prompting attempts to reverse this defect either by giving continuous inhaled nitric oxide gas, which is effective but difficult to administer, or by increasing the substrate for nitric oxide L-arginine.

PDE Inhibitors

In some embodiments, the pharmaceutical agent which is administered in addition to a nitric oxide amino acid ester compound is a PDE inhibitor. In addition to increasing the supply of nitric oxide, attempts to directly increase cyclic nucleotide second messenger levels in the smooth muscle cells have been made. Sildenafil used for erectile dysfunction blocks the enzyme phosphodiesterase type 5 present in the corpus cavernosum of the penis and also the lungs. This raises the possibility that a phosphodiesterase inhibitor, preferably a PDE type 5 inhibitor such as sildenafil, could be a relatively selective pulmonary vasodilator. There is empirical evidence supporting the inventor's selection of PDE inhibitors as a target compound in a combination therapy.

Although aerosolized prostacyclin (PGI$_2$) has been suggested for selective pulmonary vasodilation as discussed above, its effect rapidly levels off after termination of nebulization. Stabilization of the second-messenger cAMP by phosphodiesterase (PDE) inhibition has been suggested as a strategy for amplification of the vasodilative response to nebulized PGI$_2$. Lung PDE3/4 inhibition, achieved by intravascular or transbronchial administration of subthreshold doses of specific PDE inhibitors, synergistically amplified the pulmonary vasodilatory response to inhaled PGI$_2$, concomitant with an improvement in ventilation-perfusion matching and a reduction in lung edema formation. The combination of nebulized PGI$_2$ and PDE3/4 inhibition may thus offer a new concept for selective pulmonary vasodilation, with maintenance of gas exchange in respiratory failure and pulmonary hypertension. There are some reports of small clinical studies showing that such combination therapy may be efficacious in the treatment of pulmonary hypertension.

Isozymes of cyclic-3',5'-nucleotide phosphodiesterase (PDE) are a critically important component of the cyclic-3', 5'-adenosine monophosphate (cAMP) protein kinase A (PKA) signaling pathway. The superfamily of PDE isozymes consists of at least nine gene families (types): PDE1 to PDE9. Some PDE families are very diverse and consist of several subtypes and numerous PDE isoform-splice variants. PDE isozymes differ in molecular structure, catalytic properties, intracellular regulation and location, and sensitivity to selective inhibitors, as well as differential expression in various cell types.

A phosphodiesterase (PDE) inhibitor is defined herein as any drug used in the treatment of pulmonary hypertension that works by blocking the inactivation of cyclic AMP. There are five major subtypes of phosphodiesterase (PDE); the drugs enoximone (inhibits PDE IV) and milrinone (Primacor®) (inhibits PDE IIIc) are most commonly used medically. Other phosphodiesterase inhibitors include Amrinone (Inocor®) used to improve myocardial function, pulmonary and systemic vasodilation, and sildenafil (Viagra®), tadalafil (Cialis®) and vardenafil (LEVITRA®)-selective phosphodiesterase V inhibitors that are used in the treatment of erectile dysfunction. ED is a condition that affects an estimated 152 million men worldwide. Tadalafil (Cialis®) is a PDE5 inhibitor developed by Lilly ICOS LLC for the treatment of erectile dysfunction.

The composition of the present invention may also be used with a phosphodiesterase 4 (PDE4) inhibitor. The PDE4 inhibitor may be administered before or after treatment with the composition of the present invention, or it may even be added to the composition of the present invention to be administered simultaneously. The preferred PDE4 inhibitor is ibudilast, which is a neuroprotective and bronchodilator drug used mainly in the treatment of asthma and stroke. Other suitable vasodilators and/or bronchodilators include but are not limited to pirbuterol, epinephrine, salbutamol (albuterol), salmeterol, levosalbutamol (levalbuterol) ephedrine, formoterol and clenbuterol.

The composition of the present invention may also be used with a cyclooxygenase (COX) inhibitor in order to counteract a rebound response caused by withdrawal of a treatment with a composition of the present invention containing a compound of the present invention alone. The COX inhibitor may be administered before or after treatment with the composition of the present invention, or it may even be added to the composition of the present invention to be administered simultaneously. Suitable cyclooxygenase inhibitor include but are not limited to diclofenac, aceclofenac, nabumetone; meloxicam, meclofenamic, nimesulide; paracetamol; rofecoxib, celecoxib, DuP 697; GR 32191; flosulide; NS 398; L-745,337, DFU, HN-56249, JTE-552, aspirin, indometacin, and ibuprofen, or acid addition salts thereof.

Calcium Channel Blockers

In some embodiments, the pharmaceutical agent which is administered in addition to a nitric oxide amino acid ester compound is a calcium channel blocker. Calcium channel blockers, or antagonists, act by blocking the entry of calcium into muscle cells of heart and arteries so that the contraction of the heart decreases and the arteries dilate. With the dilation of the arteries, arterial pressure is reduced so that it is easier for the heart to pump blood. This also reduces the hearts oxygen requirement. Calcium channel blockers are useful for treating PPH. Due to blood pressure lowering effects, calcium channel blockers are also useful to treat high blood pressure. Because they slow the heart rate, calcium channel blockers may be used to treat rapid heart rhythms such as atrial fibrillation. Calcium channel blockers are also administered to patients after a heart attack and may be helpful in treatment of arteriosclerosis.

Calcium channel blockers which are within the scope of this invention include, but are not limited to: amlodipine (U.S. Pat. No. 4,572,909); bepridil (U.S. Pat. No. 3,962,238); clentiazem (U.S. Pat. No. 4,567,175); diltiazem (U.S. Pat. No. 3,562,257); fendiline (U.S. Pat. No. 3,262,977); gallopamil (U.S. Pat. No. 3,261,859); mibefradil (U.S. Pat. No. 4,808,605); prenylamine (U.S. Pat. No. 3,152,173); semotiadil (U.S. Pat. No. 4,786,635); terodiline (U.S. Pat. No. 3,371,014); verapamil (U.S. Pat. No. 3,261,859); aranidipine (U.S. Pat. No. 4,446,325); bamidipine (U.S. Pat. No. 4,220,649); benidipine (European Patent Application Publication No. 106,275); cilnidipine (U.S. Pat. No. 4,672,068); efonidipine (U.S. Pat. No. 4,885,284); elgodipine (U.S. Pat. No. 4,952,592); felodipine (U.S. Pat. No. 4,264,611); isradipine (U.S. Pat. No. 4,466,972); lacidipine (U.S. Pat. No. 4,801,599) lercanidipine (U.S. Pat. No. 4,705,797); manidipine (U.S. Pat. No. 4,892,875); nicardipine (U.S. Pat. No. 3,985,758); nifedipine (U.S. Pat. No. 3,485,847); nilvadipine (U.S. Pat. No. 4,338,322); nimodipine (U.S. Pat. No. 3,799,934); nisoldipine (U.S. Pat. No. 4,154,839); nitrendipine (U.S. Pat. No. 3,799,934); cinnarizine (U.S. Pat. No. 2,882,271); flunarizine (U.S. Pat. No. 3,773,939); lidoflazine (U.S. Pat. No. 3,267,104); lomerizine (U.S. Pat. No. 4,663,325); bencyclane (Hungarian Patent No. 151,865); etafenone (German Patent No. 1,265,758); and perhexiline (British Patent No. 1,025,578).

Preferred calcium channel blockers comprise amlodipine, diltiazem, isradipine, nicardipine, nifedipine, nimodipine, nisoldipine, nitrendipine, and verapamil, or, e.g., dependent on the specific calcium channel blockers, a pharmaceutically acceptable salt thereof.

The compounds to be combined can be present as pharmaceutically acceptable salts. If these compounds have, for example, at least one basic center, they can form acid addition salts. Corresponding acid addition salts can also be formed having, if desired, an additionally present basic center. The compounds having at least one acid group (for example COOH) can also form salts with bases. Corresponding internal salts may furthermore be formed, if a compound of formula comprises e.g., both a carboxy and an amino group.

In accordance with one embodiment a second generation calcium channel antagonist, such as amlodipine, is the pharmaceutical agent which is administered in addition to a nitric oxide amino acid ester compound. In some embodiments, both the nitric oxide amino acid ester compound and the calcium antagonist are administered in a sustained release dosage form. Preferably, the dosages of a nitric oxide amino acid ester compound and the calcium channel antagonist and their release form are optimized for the treatment of hypertensive patients.

The endothelin receptor antagonist (dual or selective), the modulator of prostaglandin activity, the epoprostenol derivative, the cyclooxygenase inhibitor, phosphodiesterase inhibitor and bronchodilator and the calcium channel inhibitor can be administered in the same manner as NO, i.e. by inhalation, but also by other common administration routes for pharmaceuticals. Among such routes reference can be made to sublingual, oral, and rectal administrations, application to epithelial surfaces, and injection, which may be subcutaneous, intramuscular, intravenous or intraperitoneal. Preferably, however, they are administered by inhalation.

The invention provides methods for boosting NO levels for the treatment of sickle-cell disease, pulmonary hyperthesion (e.g. pulmonary arterial hypertension, pulmonary venous hypertension), and other types of pulmonary diseases and especially acute chest syndrome associated with the disease. Inhalable composition according to the present invention can be prepared by the addition of a compound of the present invention into a suitable inhalable carrier. Inhalable carriers are chosen to target the compounds of interest to the lungs. Inhalable carriers may be liquid aerosol formulation that may contain an aqueous solvent, or a non-aqueous solvent (e.g. alcohol such as ethanol, $C_{7-18}$ hydrocarbons of a linear or branched configuration, their alcohols, and esters, as well as triglycerides), or it may be a mixture of aqueous and non-aqueous solvents. The aqueous and non-aqueous solvent may be polar (e.g. water) or non-polar (e.g. phospholipids), or mixtures thereof, as may be required for absorption of the compounds of the present invention in the lungs. The inhalable carrier (the solvent), will dissolve the compound of the present invention, an incorporate them into particles for delivery. These particles may be any suitable or effective particle, such as liposomal particles or nanoparticles.

In one embodiment of the present invention, the nitric oxide amino acid ester compound is dissolved in sterile water. A fresh dosage of the compound may be prepared every 4 to 8 hours as needed.

The inhalable carrier may also be a dry powder, such as lactose powder, microparticles or microspheres to which the compound of the present invention will be incorporated. An effective dry-powder inhalation therapy for both short and long term release of therapeutics, either for local or systemic delivery, utilizes a powder that displays minimum aggregation, as well as a means of avoiding or suspending the lung's natural clearance mechanisms until drugs have been effectively delivered.

Microparticles are convenient to administer, thereby enhancing the extent of patient compliance. In some embodiments, the microparticles may be administered in a single puff. In other embodiments, the microparticles are formulated to provide sustained release of a nitric oxide amino acid ester compound. The microparticles may facilitate local delivery of the nitric oxide amino acid ester compound to the lungs or systemic delivery via the lungs. In some embodiments, the microparticles enable less frequent dosing of the nitric oxide amino acid ester compound. For example, in some embodiments, the microparticles provide efficacious 1-10 times daily dosing of iloprost useful in the treatment of PH. In other embodiments, the microparticles permit 1-4 times or 3-4 times daily dosing of a nitric oxide amino acid ester compound. As used herein, the term "microparticle" comprising a nitric oxide amino acid ester compound and/or another pharmaceutical agent to be administered in addition to a nitric oxide amino acid ester compound includes microspheres and microcapsules, as well as microparticles, unless otherwise specified. The term "microparticle" also includes glassy formulations. Microparticles may or may not be spherical in shape.

Several sustained release delivery systems for pharmaceutical agents delivered locally to the lung or for pharmaceutical agents delivered systemically through the lungs, have been developed. One such delivery system is a formulation comprising porous microparticles, where porosity, particle geometric diameter and composition are selected and used to control the rate of release of pharmaceutical agent from the microparticles following inhalation into the lungs. It has been discovered that the composition of the microparticles (e.g., the matrix material, surfactant) can be selected to provide delayed release (and avoid the burst effect associated with immediate release formulations), and the porosity of the microparticles can be selected to provide the majority of the pharmaceutical agent release before the microparticles are removed by the pulmonary clearance mechanisms.

Although the composition of the microparticles can be selected to slow the release of the pharmaceutical agent, selection of the composition alone may not ensure that a sufficient amount of pharmaceutical agent is released before the microparticles are removed by the pulmonary clearance mechanisms. For a given composition of the microparticles, the porosity can be selected to ensure that a therapeutically or prophylactically effective amount of the pharmaceutical agent continues to be released after 2 hours, preferably such that a majority (e.g., more than about 20%, more than about 30%, more than about 40%, 50%, more than about 60%, more than about 75%, more than about 80% or more than about 90% by weight of the pharmaceutical agent) of the pharmaceutical agent is released from the microparticles by 24 hours following inhalation.

In some embodiments, the porous microparticles can provide sustained local delivery of pharmaceutical agent and/or sustained plasma levels without the need to complex the pharmaceutical agent molecule with another molecule. In addition, the sustained delivery formulations advantageously can moderate the pharmaceutical agent peaks and troughs associated with immediate release pharmaceutical agents, which can cause added toxicity or reduced efficacy.

In some embodiments, the sustained release formulations can deliver a majority of the inhaled microparticles to the appropriate region of the lung for the desired therapeutic or prophylactic use. That is, preferably, at least 50% by weight of the microparticles delivered to the lung is delivered, upon inhalation by the patient, to the appropriate region of the lung (for example, the combined central and upper lung) for the desired therapeutic or prophylactic use.

In some embodiments, the method and formulation can provide local or plasma concentrations at approximately constant values. For example, in some embodiments, they may not fluctuate by more than a factor of four over the period of sustained release.

The sustained release pharmaceutical formulations for pulmonary administration in accordance with one embodiment of the present invention include porous microparticles that comprise a nitric oxide amino acid ester compound and/or another pharmaceutical agent to be administered in addition to a nitric oxide amino acid ester compound and a matrix material. In some embodiments, the microparticle's composition, geometric diameter, and porosity provide that upon inhalation of the formulation into the lungs a therapeutically or prophylactically effective amount of a nitric oxide amino acid ester compound and/or another pharmaceutical agent to be administered in addition to a nitric oxide amino acid ester compound is released in a sustained manner from the microparticles in the lungs over a duration that extends up to at least about 2 hours, and preferably completes release by about 24 hours.

The compositions of the present invention may be administered as sprays or mists by the use of inhalable composition delivery devices that are well known in the art of inhalable compositions. The composition of the present invention is combined with a suitable propellant which will provide the force to generate the aerosol cloud. The inhalable carrier and the propellant normally form a single phase from which the aerosol and/or mist will be produced. Suitable propellants used to include chlorofluorocarbons, but since these compounds have been banned because of their effects on the ozone layer, they have been replaced with suitable compounds such as hydro-fluoroalkanes. The propellant may also be any suitable inert gas.

Suitable inhalable composition delivery devices include metered-dose inhalers and dry powder inhalers which will deliver a fixed predetermined dose of the composition of the present invention. Metered-dose inhaler are typically sealed, pressurized container, that are sealed at the time of manufacture and do not allow entry of atmospheric gasses with each activation. They also include spray pumps and nebulizers (such as the I-Neb™ or Prodose™ adaptive aerosol delivery systems, that allow the entry of air (as the propellant) into the container during and/or after every activation, and may also produce mists or droplets of varying sizes, which may be sufficient or more suitable to the treatment of certain specific diseases.

In use the patient in need of a dose of the composition according to the present invention for treating pulmonary disease (e.g. sickle-cell disease and/or acute chest syndrome) will position the inhalable composition delivery device over the oral cavity, the nasal cavity or both, and will activate the device such that it will release a dose of the composition contained therein. The aerosol spray of the composition of the present invention will then enter the airways where the aerosol spray will be absorbed by the veins or capillaries of the alveoli.

The inhalable composition of the present invention is suitable for treating pulmonary disease such as pulmonary hypertension (venous and/or arterial), sickle cell disease (and the associated acute chest syndrome), a chronic obstructive pulmonary disease (e.g. chronic bronchitis, emphysema) and pulmonary insufficiency, cystic fibrosis and Infant respiratory distress syndrome (IRDS), and pulmonary vasoconstriction or airway constriction associated with a clinical condition resulting from traumatic injury, fat embolism in the lung, acidosis, adult respiratory distress syndrome, acute mountain sickness, post cardiovascular and pulmonary surgery, acute pulmonary hypertension, persistent pulmonary hypertension of the new-born, perinatal aspiration syndrome, hyaline membrane disease, acute pulmonary thromboembolism, acute pulmonary edema, heparin-protamine reactions, hypoxia and asthma bronchiale. It is suitable for treating airways constriction associated with asthma bronchiale, acute conditions of asthma bronchiale or asthma asthmaticus.

Pulmonary hypertension is a debilitating disease characterized by an increase in pulmonary vascular resistance leading to right ventricular failure and death. Pulmonary hypertension (PH) with no apparent cause is primary pulmonary hypertension (PPH). Pulmonary hypertension includes pulmonary arterial hypertension as well as other disorders.

Importantly, the inhalable composition of the present invention is suitable for treating patients suffering from complications of sickle-cell disease, an inherited blood disorder characterized by chronic anemia and periodic episodes of pain. These patients many blood transfusions over their lifetime and may regularly need to be on ventilators in order to breathe. Acute chest syndrome is a severe manifestation of sickle cell disease. It is characterized by chest pain, fever, high blood pressure in the lung, and clogged or collapsed lungs. Abnormally shaped, or sickled, red blood cells get trapped in blood vessels in the lungs of people with the syndrome. By opening up these vessels, it is thought that nitric oxide would allow more blood cells to move through the lungs and pick up oxygen.

There are many possible explanations for nitric oxide's apparent benefits to patients with sickle-cell disease. Some studies have suggested that nitric oxide reduces the number of platelets and thus the number of blockages that deprive tissues of oxygen and lead to pain. Other research has suggested that nitric oxide may make blood cells less likely to adhere to blood-vessel walls. Also, some researchers propose that nitric oxide binds directly to hemoglobin. This reaction may prevent the protein from forming long chains, or polymerizing, and deforming cells. Also, hemoglobin may carry nitric oxide throughout the body, so the compound can have beneficial effects on a variety of tissues.

The present invention will be more readily understood by referring to the following examples which are given to illustrate the invention rather than to limit its scope.

Example 1

Water Based Aerosol Spray 1

5 to 15 mg of (2-nitrooxy)-2-ethylamino-3-methylbutanoate is dissolved in 1 ml of sterile water. The solution containing the medication is inserted into the medication chamber of a Prodose™ AAD nebulizer. The nebulizer is inserted in mouth of the patient for administration of the compound. Dosing is repeated every 4 to 8 hours, as needed. A fresh dose of the compound is preferably dissolved in sterile water.

Example 2

Water Based Aerosol Spray 2

5 to 15 mg of 2'-nitrooxyethyl 2-amino-pentanoate is dissolved in 1 ml of sterile water. The solution containing the medication is inserted into the medication chamber of a I-Neb™ AAD nebulizer. The nebulizer is inserted in mouth of the patient for administration of the compound. Dosing is repeated every 4 to 8 hours, as needed. A fresh dose of the compound is preferably dissolved in sterile water.

While preferred embodiments have been described above and illustrated in the accompanying drawings, it will be evident to those skilled in the art that modifications may be made without departing from this disclosure. Such modifications are considered as possible variants comprised in the scope of the disclosure.

The invention claimed is:
1. An inhalable composition comprising:
a therapeutically effective amount of a compound of formula (I):

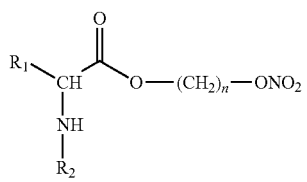

wherein
when n=1-2 and 7-10;
$R_1$ is an amino acid side chain group (D or L configuration) chosen from:
H,

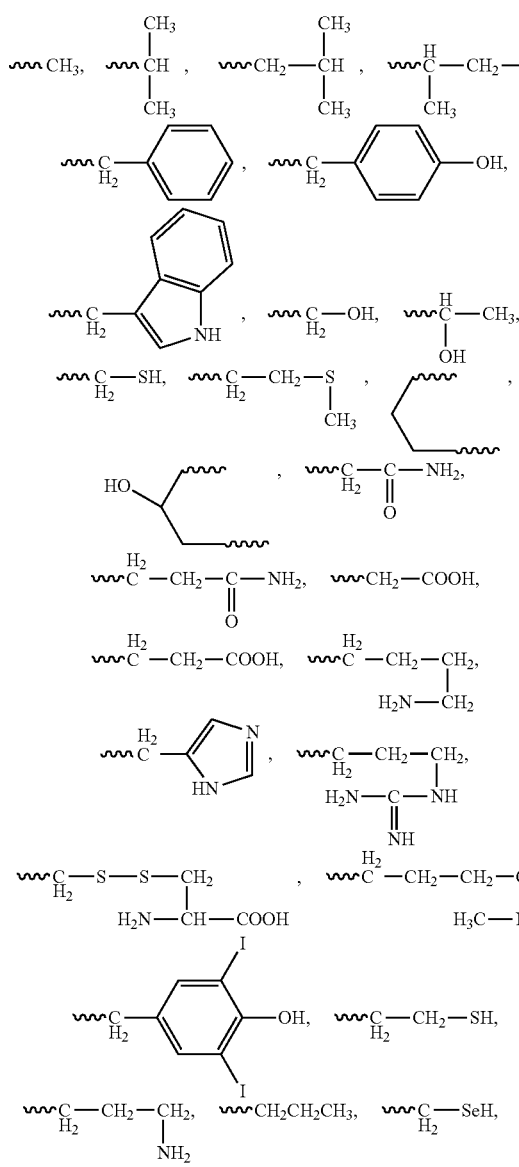

when n=3 to 6;
$R_1$=an amino acid side chain group (D or L configuration) chosen from:

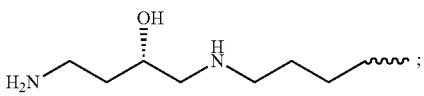

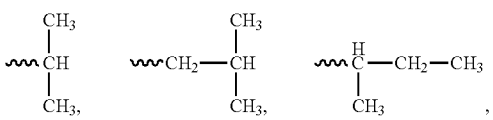

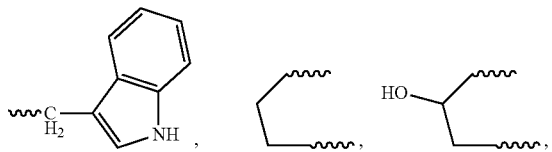

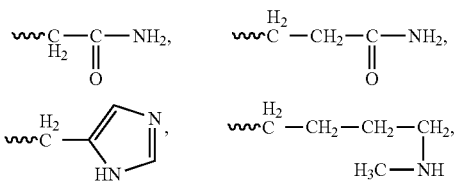

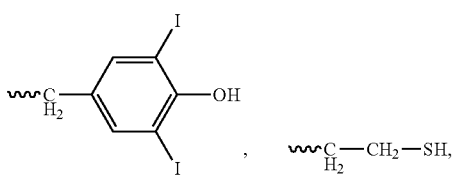

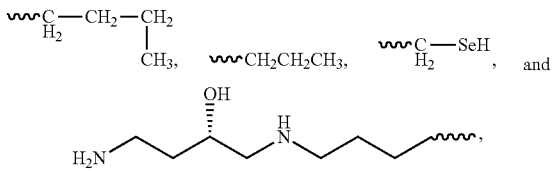

wherein when $R_1$ is

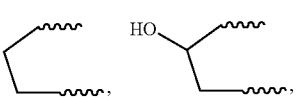

said $R_1$ is also linked to an $NH_2$ of said Formula (I) to form a proline or hydroxyproline amino acid side chain
wherein $R_2$ is a hydrogen atom, or is an amino acid of formula (II) (D or L configuration) forming a peptide bond:

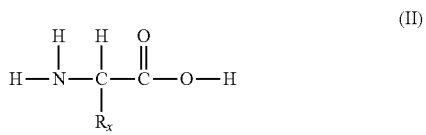

wherein $R_x$ is chosen from
H,

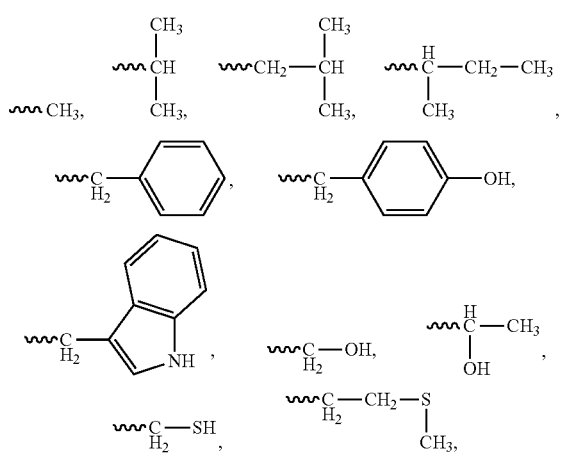

proline side chain,

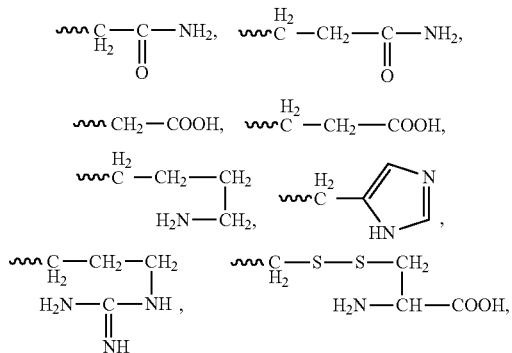

hydroxyproline side chain,

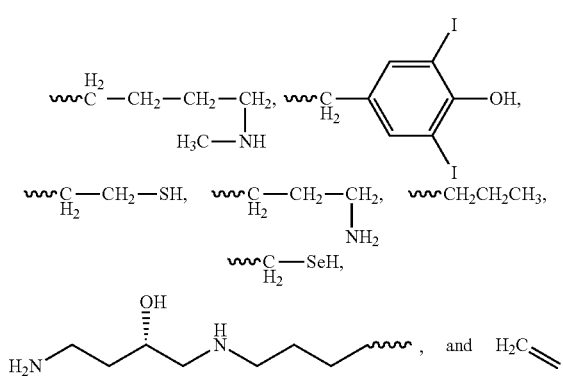

or any pharmaceutically acceptable salts thereof; and
in association with a pharmaceutically acceptable inhalable carrier.

2. The composition as claimed in claim 1, wherein said compound of formula (I) is (2-nitrooxy)-2-ethylamino-3-methylbutanoate:

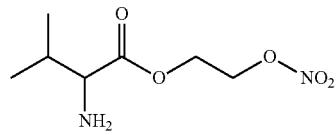

or any pharmaceutically acceptable salts thereof.

3. The composition as claimed in claim 1, wherein said compound of formula (I) is valine butylene glycol nitrate:

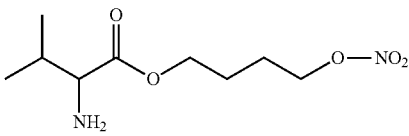 [SMILES: CC(C)C(N)C(=O)OCCCCO[N+](=O)[O-]]

or any pharmaceutically acceptable salts thereof.

4. The composition as claimed in claim 1, wherein said compound of formula (I) is 2'-nitrooxyethyl 2-amino-pentanoate:

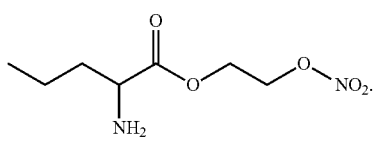

or any pharmaceutically acceptable salts thereof.

5. The composition as claimed in claim 1, wherein said compound of formula (I) is 4'-nitrooxybutyl 2-amino-pentanoate:

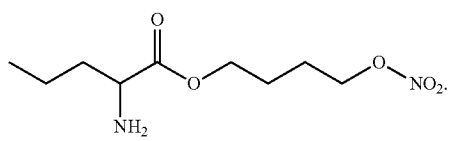 [SMILES: CCCC(N)C(=O)OCCCCO[N+](=O)[O-]]

or any pharmaceutically acceptable salts thereof.

6. The composition as claimed in claim 1, wherein said compound of formula (I) is:

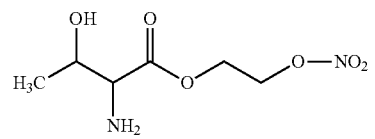

or any pharmaceutically acceptable salts thereof.

7. The composition as claimed in claim 1, further comprising a cyclooxygenase inhibitor, and wherein said cyclooxygenase inhibitor is at least one of diclofenac, aceclofenac, nabumetone; meloxicam, meclofenamic, nimesulide; paracetamol; rofecoxib, celecoxib, DuP 697; GR 32191; flosulide; NS 398; L-745,337, DFU, HN-56249, JTE-552, aspirin, indometacin, and ibuprofen, or any pharmaceutically acceptable salts thereof.

8. The composition as claimed in claim 1, further comprising an endothelin receptor antagonist, and wherein said endothelin receptor antagonist is at least one of bosentan, ambrisentan, sitaxsentan, and TBC3711.

9. The composition as claimed in claim 1, further comprising a phosphodiesterase (PDE) inhibitor, and wherein said phosphodiesterase (PDE) inhibitor is at least one of ibudilast, enoximone, milrinone, Amrinone, sildenafil, tadalafil and vardenafil.

10. The composition as claimed in claim 1, further comprising epoprostenol (prostacyclin), or an epoprostenol derivative, wherein said epoprostenol derivative is at least one of treprostinil, beraprost and iloprost.

11. The composition as claimed in claim 1, further comprising a bronchodilator, and wherein said bronchodilator is at least one of pirbuterol, epinephrine, salbutamol (albuterol), salmeterol, levosalbutamol (levalbuterol) and clenbuterol.

12. The composition as claimed in claim 1, further comprising a calcium channel blocker, and wherein said calcium channel blocker is at least one of amlodipine, bepridil, clentiazem, diltiazem, fendiline, gallopamil, mibefradil, prenylamine, semotiadil, terodiline, verapamil, aranidipine, bamidipine, benidipine, cilnidipine, efonidipine, elgodipine, felodipine, isradipine, lacidipine, lercanidipine, manidipine, nicardipine, nifedipine, nilvadipine, nimodipine, nisoldipine, nitrendipine, cinnarizine, flunarizine, lidoflazine, lomerizine, bencyclane, etafenone, and perhexiline.

13. The composition as claimed in claim 1, wherein said pharmaceutically acceptable inhalable carrier is chosen from an aqueous solvent, a non-acqueous solvent, and combinations thereof, and inhalable dry powder, a microparticle and a microsphere, wherein said aqueous and said non-aqueous solvent are chosen from a polar solvent, a non-polar solvent, and combinations thereof.

14. An inhalable composition delivery device comprising:
   at least one dose of a composition as claimed in claim 1, and
   a propellant.

15. A method of treating a pulmonary disease in a patient which comprises:
   (a) treating said patient by inhalation with a therapeutically effective amount of an inhalable composition as claimed in claim 1, wherein said pulmonary disease is at least one of a sickle cell disease, a pulmonary hypertension, a pulmonary insufficiency, a cystic fibrosis, a chronic obstructive pulmonary disease, an Infant respiratory distress syndrome (IRDS), a pulmonary vasoconstriction, and an airway constriction.

16. A method of treating a pulmonary disease in a patient which comprises:
   (a) treating said patient by inhalation with a therapeutically effective amount of an inhalable composition as claimed in claim 1, prior to or after treatment with a therapeutically effective amount of a COX inhibitor, wherein said pulmonary disease is at least one of a sickle cell disease, a pulmonary hypertension, a pulmonary insufficiency, a cystic fibrosis, a chronic obstructive pulmonary disease, an Infant respiratory distress syndrome (IRDS), a pulmonary vasoconstriction, and an airway constriction.

17. A method of treating a pulmonary disease in a patient which comprises: (a) treating said patient by inhalation with a therapeutically effective amount of an inhalable composition as claimed in claim 1, prior to or after treatment with a therapeutically effective amount of a phosphodiesterase inhibitor, wherein said pulmonary disease is at least one of a sickle cell disease, a pulmonary hypertension, a pulmonary insufficiency, a cystic fibrosis, a chronic obstructive pulmonary disease, an Infant respiratory distress syndrome (IRDS), a pulmonary vasoconstriction, and an airway constriction.

18. The method as claimed in claim 15, wherein said pulmonary disease is at least one of a sickle cell disease, a pulmonary hypertension, a pulmonary insufficiency, a cystic fibrosis, a chronic obstructive pulmonary disease, an Infant respiratory distress syndrome (IRDS), a pulmonary vasoconstriction, and an airway constriction.

\* \* \* \* \*